United States Patent
Moberg-Alehammar et al.

(10) Patent No.: US 9,445,951 B2
(45) Date of Patent: Sep. 20, 2016

(54) ABSORBENT ARTICLE HAVING IMPROVED PROPERTIES OF HANDLING LOW-VISCOSITY FECAL MATERIALS

(75) Inventors: Barbro Moberg-Alehammar, Mölndal (SE); Anna Nihlstrand, Mölndal (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 1543 days.

(21) Appl. No.: 11/819,725

(22) Filed: Jun. 28, 2007

(65) Prior Publication Data

US 2007/0255247 A1 Nov. 1, 2007

Related U.S. Application Data

(63) Continuation of application No. PCT/SE2004/002025, filed on Dec. 29, 2004.

(51) Int. Cl.
*A61F 13/511* (2006.01)
*A61F 13/495* (2006.01)

(52) U.S. Cl.
CPC .............. *A61F 13/495* (2013.01); *A61F 13/511* (2013.01); *A61F 13/5116* (2013.01); *A61F 2013/4958* (2013.01)

(58) Field of Classification Search
CPC ............ A61F 13/5116; A61F 13/5121; A61F 13/5123; A61F 2013/5127–2013/5128
USPC ................. 604/385.08, 380, 385.101, 385.19
See application file for complete search history.

(56) References Cited

U.S. PATENT DOCUMENTS

| | | | | |
|---|---|---|---|---|
| 1,829,231 A | * | 10/1931 | Mergentime | 66/170 |
| 2,902,038 A | * | 9/1959 | Bletzinger et al. | 604/365 |
| 3,038,215 A | * | 6/1962 | Harwood | 28/106 |
| 3,046,986 A | * | 7/1962 | Harwood | 604/375 |
| 3,367,333 A | * | 2/1968 | Scheier | 604/375 |

(Continued)

FOREIGN PATENT DOCUMENTS

| EP | 0 953 324 A1 | 11/1999 |
|---|---|---|
| EP | 0 969 784 B1 | 1/2000 |

(Continued)

OTHER PUBLICATIONS

International Search Report dated Sep. 8, 2005.

(Continued)

*Primary Examiner* — Paula L. Craig
(74) *Attorney, Agent, or Firm* — Buchanan Ingersoll & Rooney PC

(57) ABSTRACT

An absorbent article, such as a diaper, pant diaper, incontinence garment, incontinence insert, bed protecting sheet or the like intended to absorb and retain body exudates which may include low viscosity fecal materials. The article has an absorbent core (5) and a cover enclosing the absorbent core, the cover having a liquid pervious inner cover (6) on the body facing side of the absorbent core and a liquid impervious cover (7) on the garment facing side of the absorbent core, wherein the inner cover (6) in at least a fecal receiving area has parts of the rear and crotch portions (3, 4) of the article has a three-dimensionally structured hydrophilic fibrous web material (12) having on the body facing surface a plurality of alternating recessed (13) and elevated portions (14), wherein the recessed as well as the elevated portions are hydrophilic.

30 Claims, 5 Drawing Sheets

(56) References Cited

U.S. PATENT DOCUMENTS

| | | | | |
|---|---|---|---|---|
| 3,442,268 A * | 5/1969 | Bird | | 604/380 |
| 3,485,706 A * | 12/1969 | Evans | | 428/134 |
| 3,542,634 A * | 11/1970 | Such et al. | | 428/135 |
| 3,559,648 A * | 2/1971 | Mason, Jr. | | 604/375 |
| 3,908,659 A * | 9/1975 | Wehrmeyer et al. | | 604/374 |
| 3,965,906 A * | 6/1976 | Karami | | 604/366 |
| 3,967,623 A * | 7/1976 | Butterworth et al. | | 604/370 |
| 4,041,951 A * | 8/1977 | Sanford | | 604/375 |
| 4,079,739 A * | 3/1978 | Whitehead | | 604/365 |
| 4,276,338 A * | 6/1981 | Ludwa et al. | | 428/137 |
| 4,678,464 A * | 7/1987 | Holtman | | 604/385.03 |
| 4,704,112 A * | 11/1987 | Suzuki et al. | | 604/378 |
| 4,741,941 A * | 5/1988 | Englebert et al. | | 428/71 |
| 4,798,603 A * | 1/1989 | Meyer et al. | | 604/378 |
| 5,104,396 A * | 4/1992 | Oatley et al. | | 604/379 |
| 5,145,736 A * | 9/1992 | Kishi et al. | | 428/332 |
| 5,180,620 A * | 1/1993 | Mende | | 428/138 |
| 5,268,213 A * | 12/1993 | Murakami et al. | | 428/163 |
| 5,330,817 A * | 7/1994 | Arnott et al. | | 428/85 |
| 5,342,338 A | 8/1994 | Roe | | |
| 5,342,343 A * | 8/1994 | Kitaoka et al. | | 604/385.29 |
| 5,356,405 A * | 10/1994 | Thompson et al. | | 604/384 |
| 5,383,870 A * | 1/1995 | Takai et al. | | 604/378 |
| 5,449,352 A * | 9/1995 | Nishino et al. | | 604/383 |
| 5,505,719 A * | 4/1996 | Cohen et al. | | 604/372 |
| 5,527,300 A * | 6/1996 | Sauer | | 604/378 |
| 5,567,501 A * | 10/1996 | Srinivasan et al. | | 428/137 |
| 5,643,653 A * | 7/1997 | Griesbach et al. | | 428/120 |
| 5,670,110 A * | 9/1997 | Dirk et al. | | 264/504 |
| 5,762,641 A * | 6/1998 | Bewick-Sonntag et al. | | 604/378 |
| 5,763,044 A * | 6/1998 | Ahr et al. | | 428/138 |
| 5,853,628 A * | 12/1998 | Varona | | 264/6 |
| 5,885,264 A * | 3/1999 | Matsushita | | 604/361 |
| 5,931,823 A * | 8/1999 | Stokes et al. | | 604/358 |
| 5,957,907 A | 9/1999 | Sauer | | |
| 5,990,377 A * | 11/1999 | Chen et al. | | 604/381 |
| 6,015,936 A * | 1/2000 | Takai et al. | | 604/383 |
| 6,132,409 A * | 10/2000 | Vogt et al. | | 604/348 |
| 6,152,905 A * | 11/2000 | Osborn et al. | | 604/378 |
| 6,222,092 B1 * | 4/2001 | Hansen et al. | | 604/378 |
| 6,258,997 B1 * | 7/2001 | Johansson et al. | | 604/378 |
| 6,274,218 B1 * | 8/2001 | Shimizu | | 428/137 |
| 6,362,391 B1 * | 3/2002 | Mizutani et al. | | 604/379 |
| 6,365,794 B1 * | 4/2002 | Dabi et al. | | 604/378 |
| 6,409,715 B1 * | 6/2002 | Tanji | | 604/385.19 |
| 6,417,426 B1 * | 7/2002 | Takai et al. | | 604/378 |
| 6,423,884 B1 * | 7/2002 | Oehmen | | 604/369 |
| 6,432,094 B1 * | 8/2002 | Fujioka et al. | | 604/385.01 |
| 6,436,081 B1 * | 8/2002 | Wada et al. | | 604/385.01 |
| 6,537,936 B1 * | 3/2003 | Busam et al. | | 442/381 |
| 6,646,178 B2 * | 11/2003 | Furuya et al. | | 604/367 |
| 6,648,865 B1 * | 11/2003 | Stiehl et al. | | 604/385.01 |
| 6,648,869 B1 * | 11/2003 | Gillies et al. | | 604/385.28 |
| 6,673,418 B1 * | 1/2004 | DeOlivera et al. | | 428/171 |
| 6,692,811 B1 * | 2/2004 | Lasko | | 428/90 |
| 6,749,593 B1 * | 6/2004 | Flohr et al. | | 604/385.01 |
| 6,803,334 B2 * | 10/2004 | Mizutani et al. | | 442/394 |
| 6,878,238 B2 * | 4/2005 | Bakken et al. | | 162/362 |
| 7,105,716 B2 * | 9/2006 | Baratian et al. | | 604/367 |
| 7,153,295 B2 * | 12/2006 | Nakajima et al. | | 604/385.101 |
| 7,534,928 B2 * | 5/2009 | Sakamoto et al. | | 604/378 |
| 2001/0014796 A1 * | 8/2001 | Mizutani et al. | | 604/367 |
| 2002/0010449 A1 * | 1/2002 | Mizutani | | 604/380 |
| 2002/0013567 A1 * | 1/2002 | Mishima et al. | | 604/385.101 |
| 2002/0026168 A1 * | 2/2002 | Yagou et al. | | 604/378 |
| 2002/0028624 A1 * | 3/2002 | Mizutani et al. | | 442/394 |
| 2002/0029023 A1 * | 3/2002 | Furuya et al. | | 604/368 |
| 2002/0029024 A1 * | 3/2002 | Furuya et al. | | 604/378 |
| 2003/0026945 A1 * | 2/2003 | Lasko | | 428/131 |
| 2003/0167044 A1 * | 9/2003 | Toyoshima et al. | | 604/367 |
| 2003/0203162 A1 * | 10/2003 | Fenwick et al. | | 428/156 |
| 2004/0016091 A1 * | 1/2004 | Rivera et al. | | 28/104 |
| 2004/0106911 A1 * | 6/2004 | Roe | | 604/384 |
| 2004/0229008 A1 * | 11/2004 | Hoying | | 428/92 |
| 2005/0148967 A1 * | 7/2005 | Baratian et al. | | 604/367 |
| 2005/0148983 A1 * | 7/2005 | Doverbo et al. | | 604/385.101 |

FOREIGN PATENT DOCUMENTS

| | | | |
|---|---|---|---|
| EP | 1 035 818 B1 | | 9/2000 |
| EP | 1 236 827 A1 | | 9/2002 |
| WO | 98/36721 A1 | | 8/1998 |
| WO | 98/36722 A1 | | 8/1998 |
| WO | 99/55273 A1 | | 11/1999 |
| WO | 00/28929 A1 | | 5/2000 |

OTHER PUBLICATIONS

Written Opinion of the International Searching Authority dated Sep. 8, 2005.

* cited by examiner

ABSORBENT ARTICLE HAVING IMPROVED PROPERTIES OF HANDLING LOW-VISCOSITY FECAL MATERIALS

CROSS-REFERENCE TO RELATED APPLICATIONS

The present application is a continuation of PCT/SE2004/002025, filed on Dec. 29, 2004, and which designates the U.S. The entire contents of PCT/SE2004/002025 are incorporated herein by reference.

TECHNICAL FIELD

The present invention refers to an absorbent article, such as a diaper, pant diaper, incontinence garment and the like intended to absorb and retain body exudates which may include low viscosity fecal materials.

BACKGROUND OF THE INVENTION

Absorbent articles of the above mentioned kind comprise an absorbent core and a cover enclosing the absorbent core. The cover comprises a liquid pervious cover on the body facing side of the absorbent core, often referred to as a topsheet or liner, and a liquid impervious cover on the garment facing side of the absorbent core, often referred to as a backsheet. Bodily fluids, especially urine, easily penetrate the liquid pervious cover and are absorbed and retained by the absorbent core. Bodily exudates in solid or semi-solid state however, such as fecal materials, can not penetrate the liquid pervious cover and are normally inhibited from leaking out of the article by elasticized waistbands and leg cuffs. Additional barrier flaps are often provided between the leg openings and the absorbent core to further inhibit leakage.

It is further known to deal with fecal materials by providing a topsheet that conforms closely to the wearer and which has a large aperture that is intended to register with the anal opening, so that fecal material passes through the aperture into a void space, where it is kept isolated from the wearer. An example of such a diaper is shown in U.S. Pat. No. 5,957,907.

However these attempts do not solve the problem of handling low-viscosity fecal material that is prevalent in younger children, especially those who are breast fed. Low-viscosity fecal material easily moves around on the body facing side of the topsheet under the influence of gravity, motion and pressure by the wearer. The migration of the fecal material often moves it to the perimeter of the article, increasing the likelihood of leakage, and further smears it against the skin of the wearer making cleanup more difficult.

One attempt of dealing with low-viscosity fecal matter is described in U.S. Pat. No. 5,342,338, which discloses a topsheet having apertures large enough for low-viscosity fecal material to pass through to a secondary topsheet. The secondary topsheet immobilizes the fecal material in position for dewatering.

Another attempt is described in WO 00/28929 disclosing an apertured liner arranged as body facing cover in the rear portion of the article. In a preferred embodiment the apertured liner is a hydrophobic film laminated to fibrous layer, which provides a mechanism for absorbing and containing fecal materials which have passed through the apertured film layer.

WO 99/55273 describes an apertured laminate which is told to be adapted to handle low-viscosity fecal material. The laminate comprises first and second liquid pervious materials each having apertures with a defined effective size. The apertures of the first and second materials are aligned and the second material preferably has a hydrophilicity that is greater than the hydrophilicity of the first material.

EP-A-1 236 827 discloses an absorbent web suitable as body-side liner for absorbent articles. The web comprises a hydrophilic base sheet having a three-dimensional topography and wherein hydrophobic matter has been applied to the elevated regions. The web is told to give an improved clean, dry feel against the skin of the wearer. The problem of handling low-viscosity fecal material is not discussed in this document.

OBJECTS AND SUMMARY

An object of the present invention is to provide an absorbent article having improved properties in handling low-viscosity fecal material, especially in inhibiting low-viscosity fecal material from moving along the body facing surface of the inner cover material.

These and further objects have been achieved by the fact that the inner cover in at least a fecal receiving area comprising parts of the rear and crotch portions of the article comprises a three-dimensionally structured hydrophilic fibrous web material having on the body facing surface a plurality of alternating recessed and elevated portions, wherein the recessed as well as the elevated portions are hydrophilic.

According to one embodiment the liquid pervious inner cover comprises first and second liners, said first liner at least partially defines a front region of the body facing surface of said inner cover and said second liner at least partially defines a rear region of the body facing surface of said inner cover, wherein the second liner comprises said three-dimensionally structured hydrophilic fibrous web material.

In one aspect, hydrophilic fibers are protruding from the elevated portions of three-dimensionally structured hydrophilic fibrous web material. In a further embodiment the hydrophilic fibers are also protruding from the recessed portions of the three-dimensionally structured hydrophilic fibrous web material and/or over the entire surface area of said fibrous web.

In one aspect, apertures are provided in the recessed portions of the three-dimensionally structured hydrophilic fibrous web material.

In one aspect, the three-dimensionally structured hydrophilic fibrous web material defines the body facing surface of the inner cover in at least parts of the rear portion and crotch portion of the article that is covered by the absorbent core.

In a further aspect, the height, b, of the elevated portions, defined as the distance between the bottom of the recessed portions 13 and the tops of the elevated portions 13 is at least 0.5 mm, preferably from 0.5 to 20 mm and more preferably from 1 to 10 mm. The distance, a, between the elevated portions, defined as the shortest distance between the highest height of adjacent elevated portions, is at least 5 mm, preferably at least 10 mm and more preferably at least 15 mm. The relationship between the height, b, of the elevated portions, and the distance, a, between elevated portions is preferably: $a \geq 2 \cdot b$.

According to one embodiment, the three-dimensionally structured hydrophilic fibrous web material is absent in the front portion of the article.

In a further aspect, a material layer, which is more hydrophilic and/or has a smaller mean pore size than the three-dimensionally structured hydrophilic web material, underlies said three-dimensionally structured hydrophilic fibrous web material, so that a surface energy gradient and/or pore size gradient is created, striving to draw aqueous fluid through the three-dimensionally structured hydrophilic web material to the underlying material layer. Said underlying material layer may be a portion of the absorbent core, a portion of the first liner or another web material.

The invention is preferably applied in diapers, pant diapers and adult incontinence garments.

DESCRIPTION OF DRAWINGS

The invention will in the following be closer described with reference to some embodiments shown in the accompanying drawings.

DEFINITIONS

Absorbent Article

Figure 1:
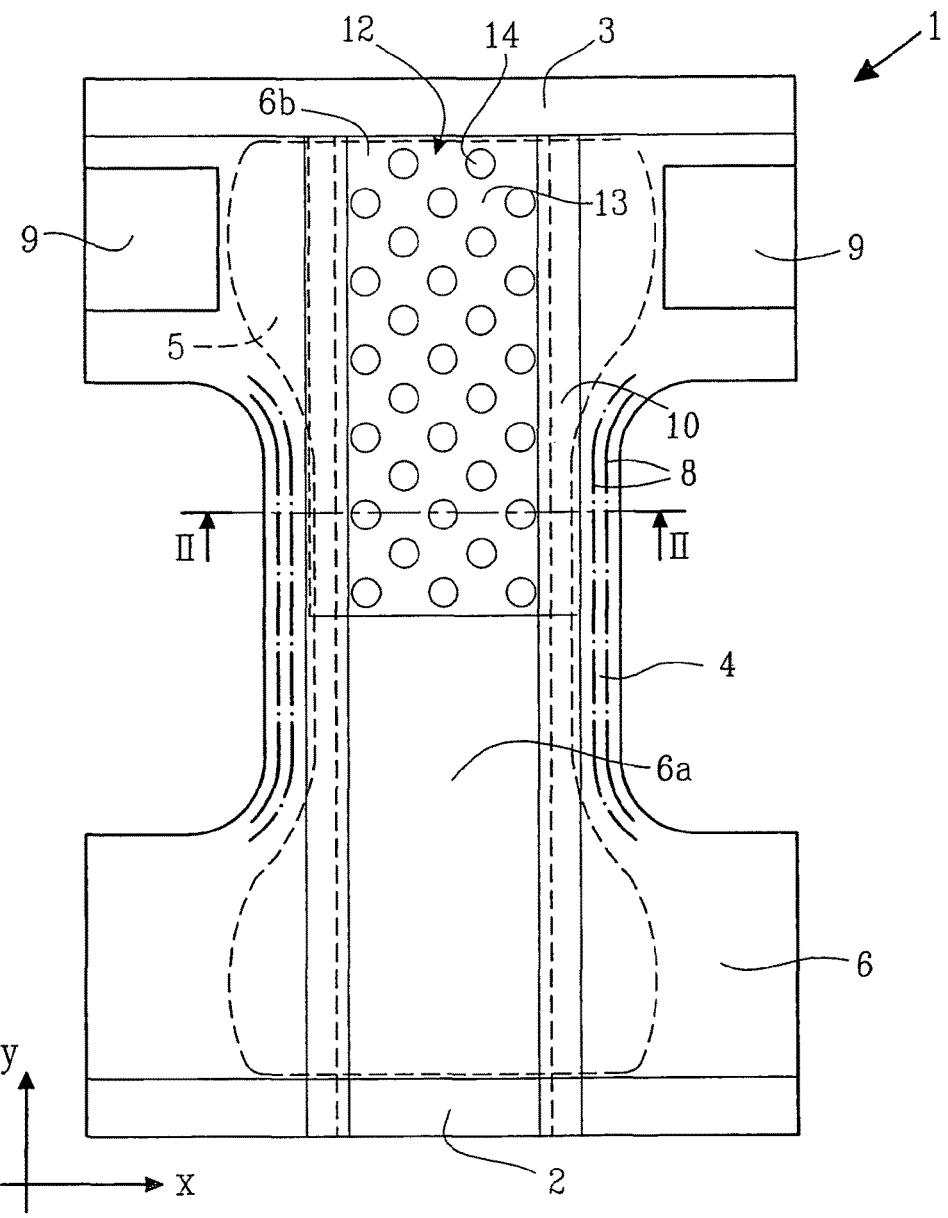
FIG. 1 shows a simplified plan view of an absorbent article in the form of a diaper in its flat, uncontracted state.
Figure 2:
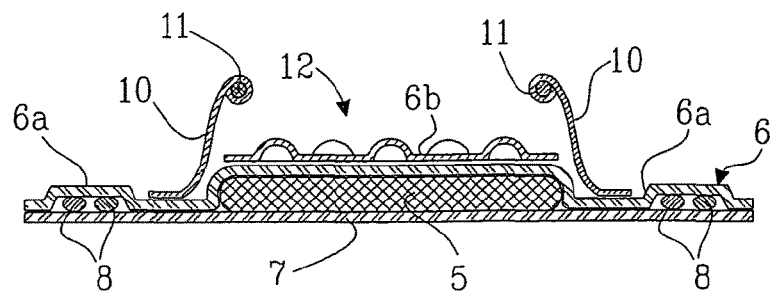
FIG. 2 is a section according to the line II-II in FIG. 1.
Figure 3:
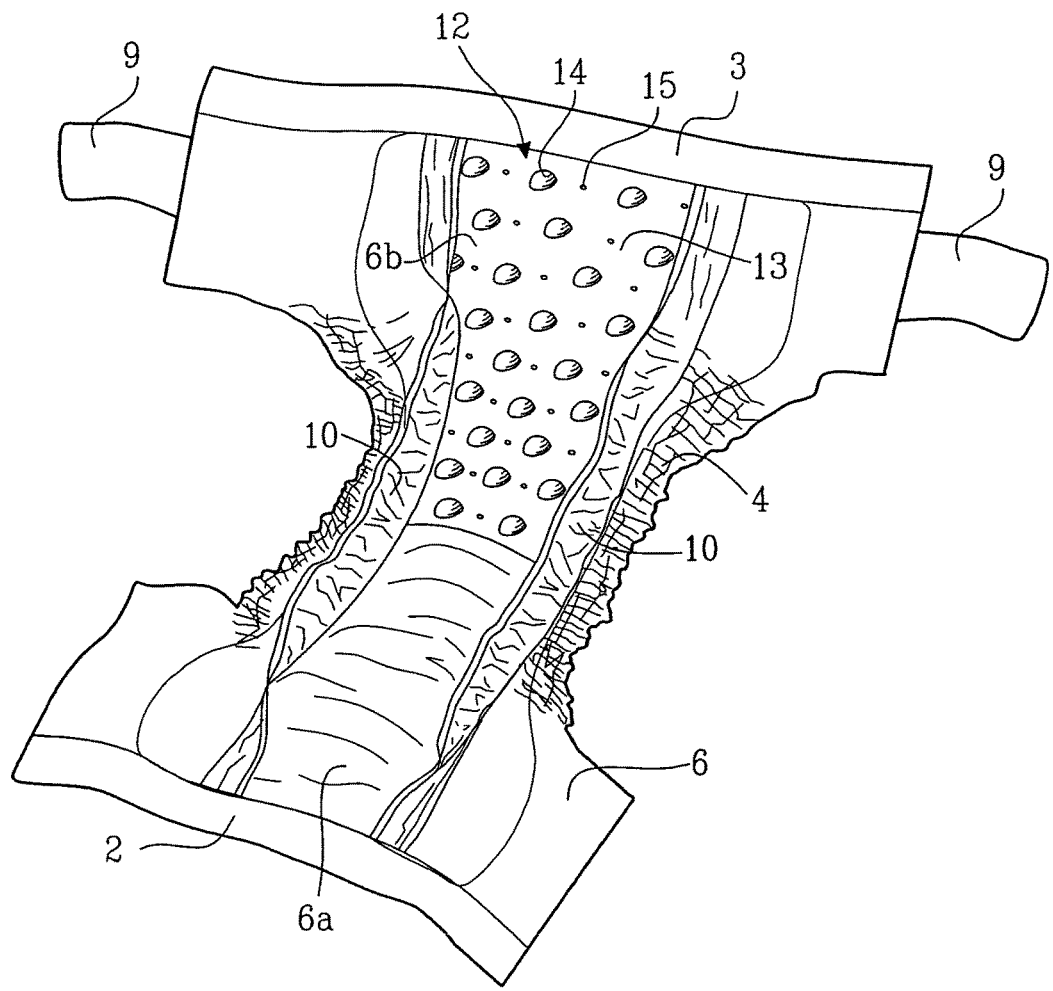
FIG. 3 shows a perspective view of a diaper in a contracted state.

The term "absorbent article" refers to products that are placed against the skin of the wearer to absorb and contain body exudates, like urine, faeces and menstrual fluid. The disclosure mainly refers to disposable absorbent articles, which are articles that are not intended to be laundered or otherwise restored or reused as an absorbent article after use.

Inner Liquid Permeable Cover

The inner liquid permeable cover forms the inner cover of the absorbent article and in use is placed in direct contact with the skin of the wearer. The inner liquid permeable cover can comprise a nonwoven material, e.g., spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc., or from a mixture of natural and manmade fibres. The inner liquid permeable cover material may further be composed of tow fibres, which may be bonded to each other in a bonding pattern, as e.g. disclosed in EP-A-1 035 818. Further examples of inner liquid permeable cover materials are porous foams, apertured plastic films etc. The materials suited as inner liquid permeable cover materials should be soft and non-irritating to the skin and be readily penetrated by body fluid, e.g. urine. The inner liquid permeable cover may further be different in different parts of the absorbent article. According to the present invention the inner liquid permeable cover comprises first and second liners, wherein the first liner at least partially defines a front region of the liquid permeable inner cover and the second liner at least partially defines a rear region of said inner cover.

Outer Liquid Impermeable Cover

The outer liquid impermeable cover forms the outer cover of the absorbent article at least on the core area thereof. The outer liquid impermeable cover can comprise a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapour to escape from the absorbent core, while still preventing liquids from passing through. Examples of breathable outer liquid impermeable cover materials are porous polymeric films, nonwoven laminates from spunbond and meltblown layers, laminates from porous polymeric films and nonwoven materials.

Absorbent Core

The "absorbent core" is the absorbent structure disposed between the two covers of the absorbent article. The absorbent core 5 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times its weight and in an aqueous solution containing 0.9 weight percent of sodium chloride. Organic materials suitable for use as a superabsorbent material include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Preferred superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core comprising a matrix of hydrophilic fibers, such as cellulosic fibers, and superabsorbent material, the proportion of superabsorbent material is preferably between 10 and 90% by weight, more preferably between 30 and 70% by weight.

It is conventional in absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers are well known in the art and may be composed of porous fibrous waddings or foam materials.

Crotch Point

Figure 7:
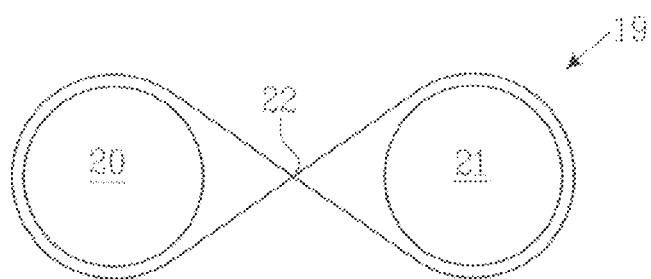
FIG. 7 illustrates how the crotch point of a wearer, and an absorbent article is determined.

The crotch point of an absorbent article and of the absorbent core of an absorbent article as defined in for example EP-B1-0 969 784, i.e. it is determined by placing the article on a wearer in a standing position and then placing an extensible filament 19 round the legs 20, 21 in a figure eight configuration (FIG. 7). The point in the article and the absorbent core corresponding to the point of intersection of the filament is deemed to be the crotch point 22. It is understood that the crotch point is determined by placing the absorbent article on the wearer in the intended manner and determining where the crossed filament would contact the article/core.

Crotch Portion

The crotch portion 4 is generally determined by first locating the crotch point 20, and then measuring forward and backward a distance of 25% of the total length of the article. Thus the crotch portion amounts to 50% of the total length of the article.

DESCRIPTION OF PREFERRED EMBODIMENTS

FIG. 1 shows a simplified plan view of an absorbent article in a flat, uncontracted state. The absorbent article shown in FIG. 1 is in the form of a diaper 1 having a longitudinal, y, and a transverse direction, x, and comprises, as seen in its longitudinal direction, a front portion 2, a rear portion 3 and a crotch portion 4 there between. In its most common form the diaper comprises an absorbent core 5 and a cover enclosing the absorbent core. Said cover comprises an inner liquid pervious cover 6 on the body facing side of the absorbent core 5 and an outer liquid impervious cover 7 on the garment facing side of the absorbent core. The inner liquid pervious cover 6 is often referred to as topsheet or liner, while the outer liquid impervious cover 7 is often referred to as backsheet.

The inner cover 6 and the outer cover 7 extend outwardly beyond the peripheral edges of the absorbent core 5 and have their inner surfaces bonded to each other, e g by gluing or welding by heat or ultrasonic. The inner and outer cover materials may further be bonded, e.g. by adhesive, to the absorbent core.

Referring to FIG. 1 the inner liquid pervious cover 6 comprises first and second liners 6a and 6b. The first liner 6a is arranged at least in the front portion 2 and the adjacent part of the crotch portion 4 and the second liner 6b is arranged at least in part of the rear portion 3 and the adjacent part of the crotch portion 4 of the diaper. The second liner 6b is arranged at least in those part of the diaper that constitutes the fecal receiving area, which is the area which immediately surrounds the point of the body facing side of the inner cover 6 that is positioned opposite the wearer's anus. The fecal receiving area is generally located in the rear portion 3 of the diaper and the rear parts of the crotch portion 4.

The second liner 6b is preferably arranged only in those parts of the rear portion 3 and the rear crotch portion 4 of the absorbent article that is covered by the absorbent core 5 and possibly the parts immediately outside the absorbent core.

The second liner 6b may alternatively cover only part of the absorbent core in the rear portion 3 and the rear crotch portion 4. The other regions of the rear portion 3 and the rear crotch portion 4 that are not covered by the absorbent core 5, such as the leg opening and the waist opening area are on their body facing surface covered by either the first liner 6a or another liner material.

It is preferred that the first and second liners overlap each other to a certain extent, so that no gaps are formed between them. According to one embodiment of the invention the first liner 6a covers the entire article and the second liner 6b overlies the first liner 6a on the body facing side in at least part of the rear portion 3 and crotch portion 4 as described above.

In an alternative embodiment the second liner 6b constitutes the inner cover or at least the body facing side of the inner cover 6 in the entire article, thus in the rear, crotch and front portions thereof.

The areas of the article adjacent the leg openings are along the longitudinal side edges provided with elastic members 8 which are bonded between the inner cover 6 and the outer cover 7 material layers in a stretched condition so as to provide elasticized leg openings of the diaper. Corresponding elastic members (not shown) may be arranged to extend in the transverse, x, direction in the front 2 and back region 3 adjacent the transverse side edges forming the waist opening of the diaper. The elastic members may alternatively be of a material that is activatable by some means, for example by heat, to an elastified state, wherein they may be attached to the article in an unstretched inactivated state and are subsequently activated to a contracted elastic state.

The rear portion 3 is provided with fasteners 9 attached thereto. The fasteners 9 are intended to be fastened to the front portion of the article to form a pant-like shape. The fasteners 9 may be in the form of adhesive tapes or hook elements adapted to attach to a loop material, for example in the form of a nonwoven material forming the outer coversheet of the diaper.

The diaper is further provided with elastic barrier flaps 10 having a proximal edge and a distal edge, and an elastic member 11 contractably attached at the respective distal edge, thus spacing the distal edge of the barrier flaps 10 from the inner cover 6. Alternatively the elastic members 11 are of the activatable kind as described above, wherein they may be attached to the barrier flaps in an uncontracted position and be activated subsequently. The barrier flaps 10 form leakage barriers and are at their proximal edge secured to the inner cover 6 outside or above the absorbent core 5.

The first liner 6a may be any material suited as inner liquid pervious cover as described above in the definition. The second liner 6b is of a fibrous web material 12 that has a clearly visible three-dimensional structure of alternating recessed 13 and elevated portions 14. The height of the elevated portions, defined as the distance, b, between the bottom of the recesses and the tops of the elevated portions is at least 0.5 mm, preferably from 0.5 to 20 mm and more preferably from 1 to 10 mm.

The distance between the elevated portions is at least 5 mm, preferably at least 10 mm and more preferably at least 15 mm. The distance, a, between the elevated portions is defined as the shortest distance between the highest height of adjacent elevated portions. This is illustrated in FIGS. 4a-d.

The relationship between the height, b, and the distance, a, is preferably: $a \geq 2 \cdot b$.

The height, b, the distance, a, as well as the relationship between b and a may be the same or different in different areas of the second liner 6b.

The second liner 6b is of a hydrophilic fibrous material 12, which is either inherently hydrophilic or rendered hydrophilic by treatment with a surfactant or by other means, for example corona treatment.

The term "hydrophilic" in this context means that the material has an affinity for being wetted by water, which generally means that it has a contact angle for water that is less than 90°.

Examples of suitable materials for use as second liner 6b are different types of nonwoven materials, such as spunbond webs, meltblown webs, carded webs, thermobonded webs, through-air-bonded webs etc. Airlaid mixtures of cellulosic fibers and mixtures of cellulosic and synthetic fibers may be used, said airlaid mixture being bonded by latex or by thermobonding. Wetlaid tissue paper, which optionally may contain a certain amount of synthetic fibers may further be used as second liner. Laminates of the above mentioned material are also feasible. The three-dimensional shaping of the fibrous sheet material may be accomplished by any method known in the art, such as vacuum forming, heat embossing or printing with a bonding agent, such as latex or by other means.

The elevated portions 14 or the recessed portions 13 or both the elevated and the recessed portions may be formed by impressions made in a fibrous sheet material.

According to a further embodiment of the invention the three-dimensional structure of the material used as second liner 6b is accomplished by a flocking technique, wherein fibers 17 are applied and secured in an upright position onto a carrier web 18, so as to protrude therefrom. This is illustrated in FIG. 4d. The fibers 17 are applied only in certain areas so as to form groups of fibers, each group forming an elevated portion 14, and wherein fiber free areas, forming recessed portions 13 are provided between said groups of fibers. Flocked materials of this kind are disclosed in for example WO 98/36722 and WO 98/36721.

Figure 4A:
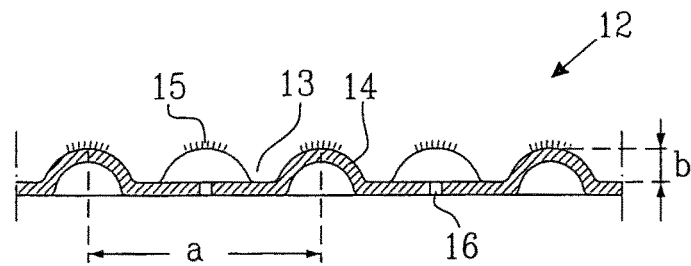
FIGS. 4a-d are sections through three embodiments of three-dimensional web materials used as a second liner according to an embodiment of the invention.

In the embodiment shown in FIG. 4a fibers 15 are protruding from the elevated portions 14. These fibers 15 are also hydrophilic and may be of the same type of fibers that constitutes the fibrous web 12 of the second liner 6b or they may be different fibers. The fibers 15 may be attached to the fibrous web 12 forming the second liner 6b by thermal fusion, chemical bonding through the use of a binder agent or adhesive, entanglement, electrostatic attachment or the like. In case the fibers 15 are fibers contained in the fibrous web 12 forming the second liner 6b, fiber ends may be caused to protrude from the surface of the elevated portions 14 by mechanical brushing or other treatment, which causes fiber ends to be released from the web and to protrude from the surface thereof, while the opposite ends of the fibers still remain attached to the web.

The web 12 shown in FIG. 4a further has apertures 16 in the recessed portions 13. These apertures 16 have an effective size of at least 5 mm$^2$, preferably at least 10 mm$^2$. The apertures 16 can vary in size, shape and pattern. Examples of possible shapes include, but are not limited to, circular, square, rectangular, oval, triangular etc. They may be arranged either in a uniform or random pattern and be distributed regularly over the surface area of the second liner or be distributed with a smaller distance in certain parts of the second liner than in other parts thereof.

Figure 4B:
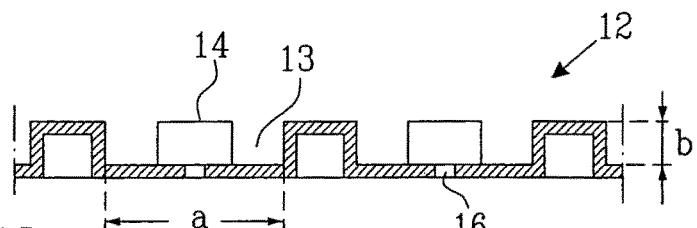
Figure 4C:
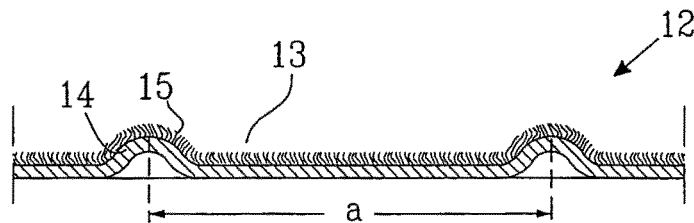
Figure 4D:
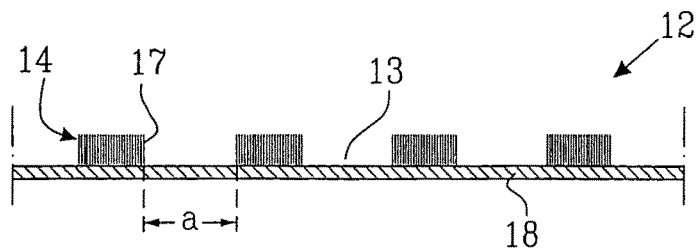

The web 12 shown in FIG. 4a has a substantially sinusoidal cross sectional shape, while the web shown in FIG. 4b has a substantially square wave cross sectional shape. In FIG. 4c there is a relatively large distance, a, between the elevated portions 14. The web 12 further has fibers 15 protruding from the surface both from the elevated portions 14 and the recessed portion 13. The web 12 shown in FIG. 4c has no apertures made therein. Preferably it has a porosity that is sufficient to provide at least a certain degree of dewatering effect and storing effect on low-viscosity fecal material. Because of the large recessed area 13, the web in FIG. 4c has a relatively large fecal receiving volume.

FIG. 4d shows a substantially planar carrier web material 18 onto which groups of fibers 17 have been flocked so as to create elevated regions 14, in the manner disclosed above. The fibers 17 as well as the carrier web material 18 are hydrophilic. The method of flocking the fibers 17 onto the carrier web 18 may be any known in the art, such as electrostatic, mechanical or combinations thereof. The fibers 17 are secured to the carrier web material by thermal fusion, mechanical entangling, hydroentangling or by chemical bonding through the use of a binder agent or adhesive or by other means.

Figure 5:
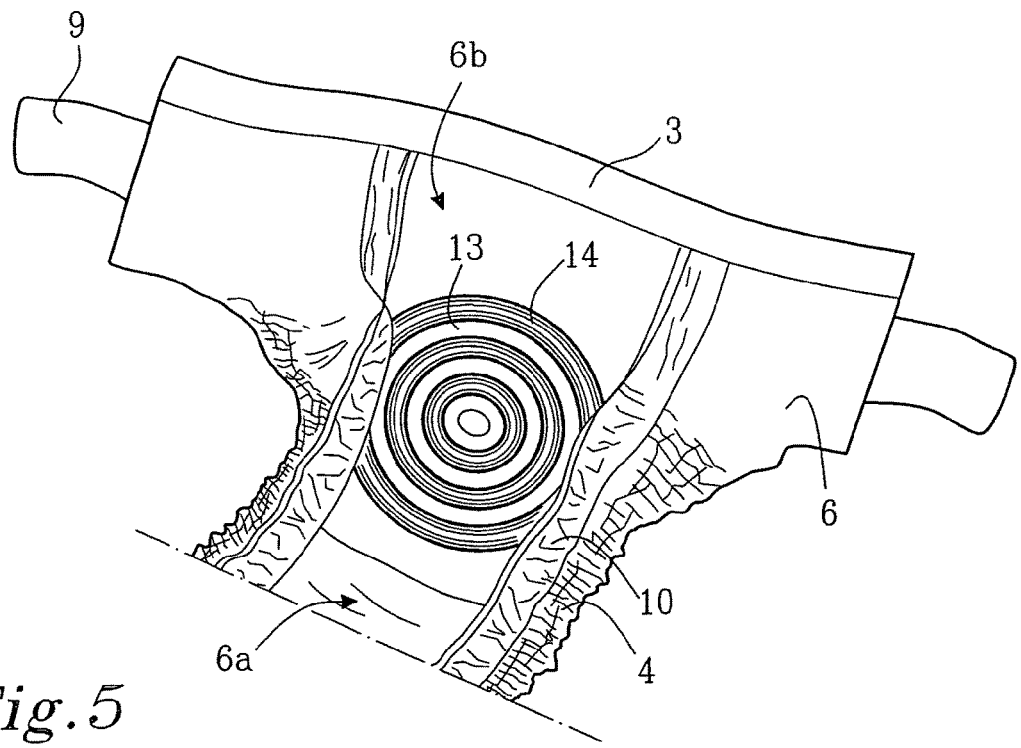
FIGS. 5 and 6 are plan views of further embodiments of diapers according to the invention.
Figure 6:
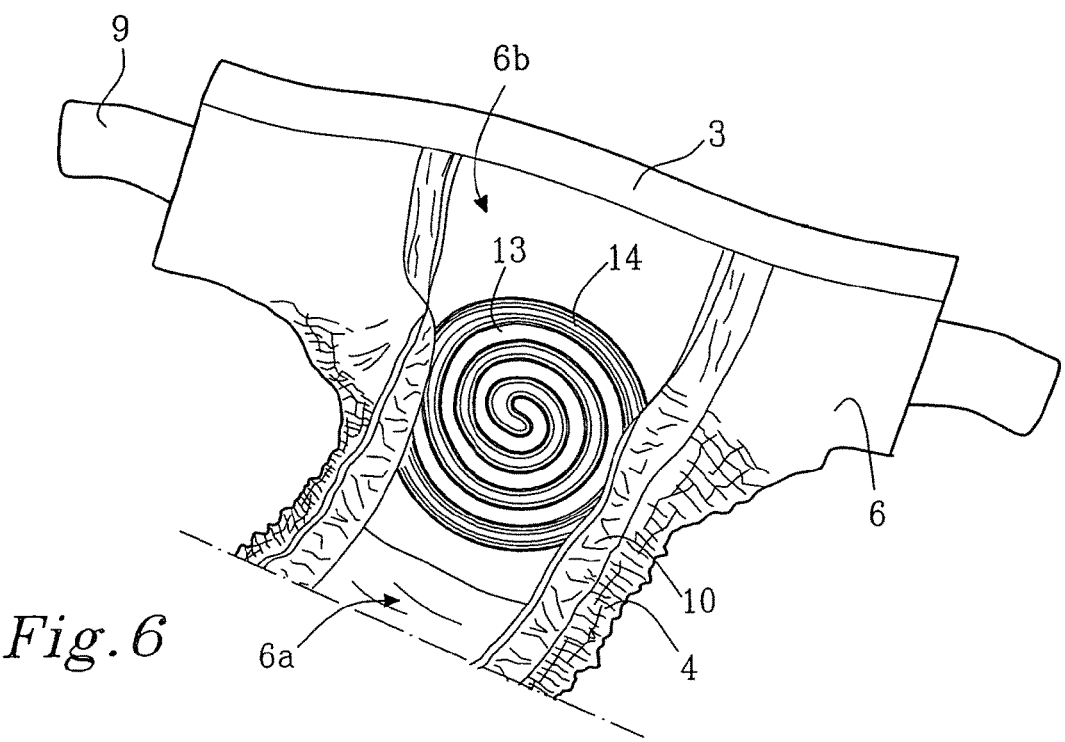

The elevated portions 14 may, as seen in a plan view from above, have any pattern and form any group of pattern that is appropriate for the intended purpose. As is shown in FIG. 1 the elevated portions 14 are in the form of bosses protruding from a surface forming the recessed portions 13. In FIG. 5 the elevated portions 14 are in the form of annular concentric ridges with valleys there between forming the recessed portions 13. In FIG. 6 the ridges and valleys are arranged in a spiral pattern. The elevated portions 14 may further form lateral ridges adjacent the side edges of the second liner 6b, while the entire central area of the second liner 6b forms a recessed portion 13. This is illustrated in FIG. 4c.

A fibrous web material 12 as disclosed above used as second liner 6b is especially effective in handling low-viscosity fecal material, which is prevalent in younger children, especially those who are breast fed, and also in wearer's having diarrhea. Such low-viscosity fecal material easily moves around the body facing side of the inner cover and increases the risk for leakage, and further smears it against the skin of the wearer making cleanup more difficult.

FIG. 7 illustrates how the crotch point 20 of an absorbent article is determined by placing the article on a wearer in a standing position and then placing an extensible filament 19 around the legs 20, 21 in a figure eight configuration. As mentioned above the crotch portion 4 is generally determined by first locating the crotch point 22, and then measuring forward and backward a distance of 25% of the total length of the article. Thus the crotch portion 4 amounts to 50% of the total length of the article.

Figure 8:
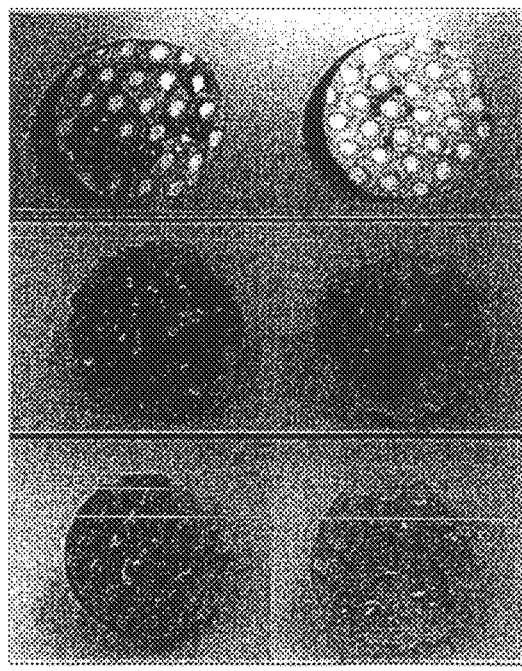
FIG. 8 shows photos of samples of hydrophilic and hydrophobic fibrous webs having remaining low viscosity faeces applied thereto.

It has been shown that low-viscosity fecal material adheres more effectively to a hydrophilic than to a hydrophobic structured fibrous web 12 as seen in FIG. 8. This results in an immobilization of the faeces preventing it from moving around on the body facing side of the topsheet under the influence of pressure and motion of the wearer. A more effective dewatering of the low-viscosity fecal material, which may contain high amounts of water, sometimes more than 90% water, is also accomplished.

Figure 9:
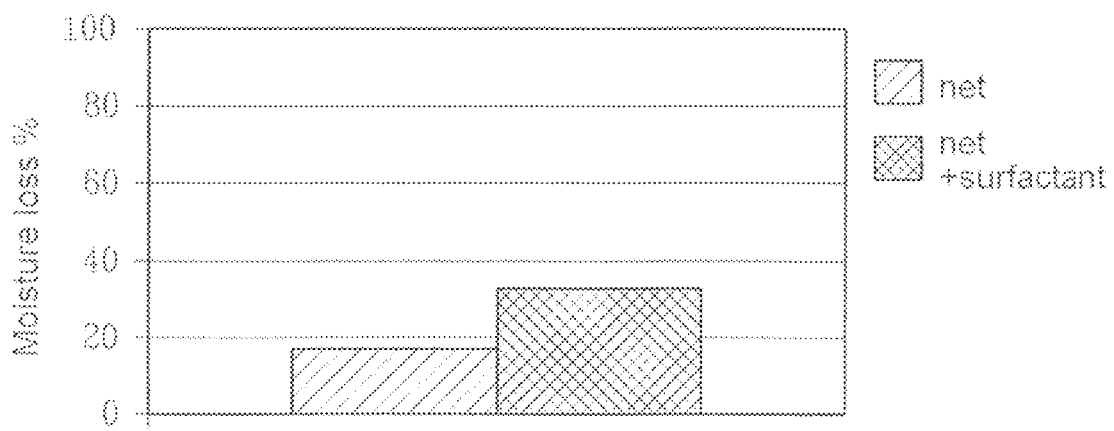
FIG. 9 illustrates the dewatering effect on low-viscosity faeces of fibrous webs having different degrees of hydrophilicity.

This effect is illustrated in FIGS. 8 and 9. These tests do however not form part of the present invention and are only referred to as illustrating the effect of a hydrophilic material as compared to a less hydrophilic or a hydrophobic material. The test illustrated in FIG. 8 measures the adhesiveness of faeces to a hydrophilic fibrous web as compared to a hydrophobic fibrous web. Low viscosity natural faeces samples from three different breast fed babies were used in this test. The sample of faeces was placed in a glass beaker having a diameter of 37 mm and fixed in an instrument of the type Instron Corporation 5542, measuring cell 500N, Series IX software. A test material was mounted on the entire underside of a flat, circular probe, diameter 25 mm. The probe was lowered towards the faeces until the whole area of the material mounted on the probe (4.9 cm$^2$) was in contact with the faeces sample. The probe was thereafter raised (5 mm/s) and the force was registered. After failure, within the faeces sample and/or between the faeces sample and the material mounted on the probe, photographs of the material-covered probe with remains of faeces were taken. These photos are shown in FIG. 8.

Two different test materials were used in the tests. The first one, which is shown to the right in all photos was a hydrophobic SMS (spunbond-meltbond-spunbond) nonwoven, basis weight 19 gsm, available from Tredegar, Italy (material code 8,210,166) and the material shown to the left was a through-air-bonded hydrophilic nonwoven, basis weight 18 gsm, also available from Tredegar, Italy (material code 8,210, 167). The materials had apertures and had a slight three-dimensional structure, which however is not sufficient for the purpose of this invention. The tests anyhow show that the hydrophilic nonwoven shown to the left in the photos had a higher adhesiveness of faeces than the hydrophobic nonwoven shown to the right. It is pointed out that the same faeces samples were used in pairs on the left and right materials in the upper row, the middle row and the lower row respectively on the photos.

Adherence of the faeces to the fibrous web means that the faeces will be immobilized and not move easily around on the material, which reduces the leakage risk.

Hydrophilic fibers 15 or 17 protruding from the surface of the hydrophilic web 12, especially from the elevated portions 14 thereof reinforce the inhibiting effect on the low viscosity faeces to move around on the surface of the web. Apertures 16 in the recessed portions 13 will increase the dewatering effect. This dewatering effect will become even more effective if the underlying material layer is more hydrophilic and/or has a smaller effective pore radius as measured by PVD (pore volume distribution) measurements, and thus a higher capillary action effect, than the hydrophilic web material 12 forming the second liner 6b, so that a surface energy gradient and/or pore size gradient is created striving to draw aqueous fluid through the second liner to the underlying material layer, which may be the absorbent core, a portion of the first liner 6a underlying the second liner 6b or another liner material underlying the second liner 6b. PVD measurements are performed by means of a PVD apparatus manufactured by Textile Research Institute, Princeton, USA. The function of the PVD apparatus is described in detail in Miller, B. and Tyomkin, L. Textile Research Journal 56(1986) 35.

FIG. 9 shows the dewatering effect on low-viscosity faeces of fibrous webs of different hydrophilicity. The measuring cups used in this test are manufactured of Plexiglas and consist of one upper and one lower cylinder and are especially suited for small sample quantities. In the standard model, a polyamide net (Monodur PA 710 µm, available from AB Derma, Box 4147, Gråbo, Sweden) was fastened with glue to the bottom of the upper cylinder. The lower cylinder was equipped with a beveled bottom where the liquid from the faeces sample was collected. A faeces sample of approximately 3 g was added to the upper cylinder (exact amount was noted). The lower cylinder was also weighed and the result noted. The two cylinders were then put together and the measuring cup with faeces was centrifuged in a Beckham GP centrifuge at a speed of 214 g for 10 minutes. After centrifugation the lower cylinder of the measuring cup was removed and weighed. The liquid that pass from the upper to the lower cylinder was thereafter calculated.

FIG. 9 shows the results from a test in which faeces from one breast-fed four-month old baby (one emptying) was used. In this test standard model nets were used, but prior to usage, one of the two nets was dipped into a bath with surfactant (Brillo, Johnson wax professional, Box 24, 164 93 Kista, Sweden) and thereafter air-dried. The centrifugation conditions were as described above.

The tests show that more of the faeces material passes through the more hydrophilic net material. Although the net materials used in the tests were not of the three-dimensionally structured type as claimed in the present invention, the test shows the improved dewatering effect of the more hydrophilic of the two otherwise identical net materials.

In all the examples a so called open diaper is shown, but it is evident that the invention may be applied also to so called pant diapers, in which the front and back portions 2 and 3 are joined to each other along their longitudinal side edges thereof forming side seams to define a waist-opening and a pair of leg-openings. It may also be applied to incontinence garments and incontinence inserts for adults and in bed protection sheets.

Furthermore, the invention is not restricted to the above-mentioned illustrative embodiments, but is naturally applicable to other embodiments within the scope of the following patent claims, and equivalents thereof.

The invention claimed is:

1. An absorbent article comprising:
    an absorbent core and a cover enclosing the absorbent core, the absorbent core including opposed longitudinal edges extending in a longitudinal direction of the absorbent article,
    said cover comprising a liquid pervious inner cover on the body facing side of the absorbent core and a liquid impervious outer cover on the garment facing side of the absorbent core, said article having in the longitudinal direction a front portion, a rear portion and a crotch portion therebetween, the inner cover, in at least a fecal receiving area, comprises parts of the rear and crotch portions of the article, and the inner cover comprises a nonwoven three-dimensionally structured hydrophilic fibrous web material having on the body facing surface a plurality of alternating recessed and elevated portions,
    wherein the recessed as well as the elevated portions are hydrophilic and said three-dimensionally structured hydrophilic fibrous web material defines the body facing surface of the inner cover in at least parts of the rear portion and crotch portion of the article that is covered by the absorbent core,
    the liquid pervious inner cover comprises first and second liners, said first liner at least partially covers a front region of the body facing surface of said inner cover, and said second liner overlaps the first liner and at least partially covers a rear region of the body facing surface of said first liner in the rear region only in an area of the rear region that overlaps the absorbent core, and extends to longitudinal edges of the absorbent core at least in the crotch portion without crossing the longitudinal edges in the crotch portion,
    said second liner comprises a continuous sheet of said nonwoven three-dimensionally structured hydrophilic fibrous web material and covers a smaller area of the absorbent core than the first liner as viewed in plan view of the article in a flat, uncontracted state of the article, and
    apertures are provided in the recessed portions of the three-dimensionally structured hydrophilic fibrous web material, each aperture extending continuously from the body facing surface of the second liner to the first liner.

2. The absorbent article as claimed in claim 1, wherein hydrophilic fibers protrude from the elevated portions of said three-dimensionally structured hydrophilic fibrous web material.

3. An absorbent article as claimed in claim 2, wherein hydrophilic fibers protrude from the recessed portions of said three-dimensionally structured hydrophilic fibrous web material.

4. An absorbent article as claimed in claim 2, wherein hydrophilic fibers protrude from the entire surface area of said three-dimensionally structured hydrophilic fibrous web material.

5. The absorbent article as claimed in claim 1, wherein the height of the elevated portions, defined as the distance between the bottom of the recessed portions and the tops of the elevated portions, is at least 0.5 mm.

6. The absorbent article as claimed in claim 5, wherein the distance between the elevated portions, defined as the shortest distance between the highest height of adjacent elevated portions, is at least 5 mm.

7. The absorbent article as claimed in claim 6, wherein the distance between the elevated portions, defined as the shortest distance between the highest height of adjacent elevated portions, is at least 10 mm.

8. The absorbent article as claimed in claim 6, wherein the distance between the elevated portions, defined as the shortest distance between the highest height of adjacent elevated portions, is at least 15 mm.

9. The absorbent article as claimed in claim 6, wherein the distance between elevated portions is greater than or equal to twice the height of the elevated portions.

10. The absorbent article as claimed in claim 1, wherein the height of the elevated portions, defined as the distance between the bottom of the recessed portions and the tops of the elevated portions, is 0.5 to 20 mm.

11. The absorbent article as claimed in claim 1, wherein the height of the elevated portions, defined as the distance between the bottom of the recessed portions and the tops of the elevated portions, is 1 to 10 mm.

12. The absorbent article as claimed in claim 1, wherein said three-dimensionally structured hydrophilic fibrous web material is absent in the front portion of the article.

13. The absorbent article as claimed in claim 1, wherein a material layer underlying the three-dimensionally structured hydrophilic fibrous web material is more hydrophilic and/or has a smaller mean pore size than said three-dimensionally structured hydrophilic web material, so that a surface energy gradient and/or a pore size gradient is created, striving to draw aqueous fluid through the three-dimensionally structured hydrophilic web material to the underlying material layer.

14. The absorbent article as claimed in claim 13, wherein said underlying material layer is a portion of the absorbent core, a portion of the first liner or another web material.

15. The absorbent article as claimed in claim 1, wherein said article is a diaper, a pant diaper, an incontinence garment, an incontinence insert or a bed protection sheet.

16. The absorbent article as claimed in claim 1, wherein the elevated portions are in the form of annular concentric ridges and the recessed portions are valleys between the ridges.

17. The absorbent article as claimed in claim 1, wherein the elevated portions are in the form of ridges arranged in a spiral pattern, and the recessed portions are valleys between the ridges.

18. The absorbent article as claimed in claim 1, wherein hydrophilic fibers protrude from the top surface of said three-dimensionally structured hydrophilic fibrous web material.

19. The absorbent article as claimed in claim 1, wherein the elevated portions are in the form of bosses protruding from the surface forming the recessed portions.

20. The absorbent article as claimed in claim 1, wherein the absorbent core has a substantially uniform thickness.

21. The absorbent article as claimed in claim 1, wherein the garment facing surface of the three-dimensionally structured hydrophilic fibrous web material is planar across the center of the absorbent core.

22. The absorbent article as claimed in claim 1, wherein the first liner covers the entire article and the second liner overlies the first liner on the body facing surface of the inner cover in at least part of the rear portion and the crotch portion.

23. The absorbent article as claimed in claim 1, further comprising:
a transverse direction perpendicular to the longitudinal direction;
wherein the elevated portions are staggered relative to each other, such that each of at least some of the elevated portions are offset with respect to a closest adjacent elevated portion in both the longitudinal and transverse directions of the absorbent article.

24. The absorbent article as claimed in claim 1, wherein the minimum effective pore size of each of the apertures is 5 $mm^2$.

25. The absorbent article as claimed in claim 1, wherein the minimum effective pore size of each of the apertures is 10 $mm^2$.

26. The absorbent article as claimed in claim 1, wherein apertures are not provided in the elevated portions of the three-dimensionally structured hydrophilic fibrous web material.

27. The absorbent article as claimed in claim 1, wherein the second liner includes a planar section between the elevated portions, the elevated portions protruding upwardly from the planar section in a direction away from the body facing side of the absorbent core.

28. An absorbent article comprising:
an absorbent core and a cover enclosing the absorbent core, said cover comprising a liquid pervious inner cover on the body facing side of the absorbent core and a liquid impervious outer cover on the garment facing side of the absorbent core, said article having in a longitudinal direction a front portion, a rear portion and a crotch portion therebetween, the inner cover, in at least a fecal receiving area, comprises parts of the rear and crotch portions of the article, and the inner cover comprises a three-dimensionally structured hydrophilic fibrous web material having on the body facing surface a plurality of alternating recessed and elevated portions, wherein the three-dimensionally structured hydrophilic fibrous web material is absent in the front portion and in at least a part of the crotch portion of the article in an area over a longitudinal centerline of the article,
wherein the recessed as well as the elevated portions are hydrophilic and said three-dimensionally structured hydrophilic fibrous web material defines the body facing surface of the inner cover in at least parts of the rear portion and crotch portion of the article that is covered by the absorbent core,
the liquid pervious inner cover comprises first and second liners, said first liner at least partially covers a front region of the body facing surface of said inner cover, and said second liner overlaps the first liner and at least partially covers a rear region of the body facing surface of said inner cover,
said second liner comprises said three-dimensionally structured hydrophilic fibrous web material and covers a smaller area of the absorbent core than the first liner as viewed in plan view of the article in a flat, uncontracted state of the article, and
at least a portion of the second liner comprises hydrophilic fibers each having one free end protruding from a body facing surface of the second liner, and an opposing end fixed to the second liner.

29. An absorbent article comprising:
an absorbent core and a cover enclosing the absorbent core, said cover comprising a liquid pervious inner cover on the body facing side of the absorbent core and a liquid impervious outer cover on the garment facing side of the absorbent core, said article having a front portion, a rear portion and a crotch portion therebetween, the inner cover, in at least a fecal receiving area, comprises parts of the rear and crotch portions of the article, and the inner cover comprises a nonwoven three-dimensionally structured hydrophilic fibrous web material having on the body facing surface a plurality of alternating recessed and elevated portions, wherein the recessed as well as the elevated portions are hydrophilic and said three-dimensionally structured hydrophilic fibrous web material defines the body facing surface of the inner cover in at least parts of the rear portion and crotch portion of the article that is covered by the absorbent core, the liquid pervious inner cover comprises first and second liners, said second liner overlaps the first liner in the rear portion only in an area of the rear portion that is covered by the absorbent core, and comprises a continuous sheet of said nonwoven three-dimensionally structured hydrophilic fibrous web material, said second liner includes a planar section between the elevated portions, the elevated portions protruding upwardly from the planar section in a direction away from the body facing side of the absorbent core, and apertures are provided in the recessed portions of the three-dimensionally structured hydrophilic fibrous web material, wherein the minimum effective pore size of each of the apertures is 5 mm$^2$.

30. The absorbent article as claimed in claim 29, wherein the effective pore size of each of the apertures is 10 mm$^2$.

\* \* \* \* \*